(12) United States Patent
Little et al.

(10) Patent No.: US 6,652,100 B1
(45) Date of Patent: Nov. 25, 2003

(54) RETINOSCOPE WITH MAGNETIC COUPLING

(75) Inventors: Mervyn Aubrey Little, Camberley (GB); James Robert Arnold Matthews, Bracknell (GB)

(73) Assignee: Keeler Limited, Windsor (GB)

( * ) Notice: Subject to any disclaimer, the term of this patent is extended or adjusted under 35 U.S.C. 154(b) by 43 days.

(21) Appl. No.: 10/030,291

(22) PCT Filed: Jun. 20, 2000

(86) PCT No.: PCT/GB00/02392

§ 371 (c)(1),
(2), (4) Date: Apr. 15, 2002

(87) PCT Pub. No.: WO01/00081

PCT Pub. Date: Jan. 4, 2001

(30) Foreign Application Priority Data

Jun. 25, 1999 (GB) ............................................. 9914818

(51) Int. Cl.⁷ ................................................ A61B 3/10
(52) U.S. Cl. ..................................................... 351/211

(58) Field of Search ................................ 351/200, 205, 351/211–216, 218, 221

(56) References Cited

U.S. PATENT DOCUMENTS 3,439,978 A * 4/1969 Moore et al. ................ 351/211
5,189,449 A * 2/1993 Perkins ........................ 351/211

* cited by examiner

*Primary Examiner*—George Manuel
*Assistant Examiner*—John R Sanders
(74) *Attorney, Agent, or Firm*—Barnes & Thornburg

(57) ABSTRACT

A streak retinoscope projects an elongate patch of light onto the retina of an eye under examination. A housing (1) contains means for rotating the patch relative to the eye and adjustable focusing means for focusing the patch on the eye. Both the rotation means and the focusing means are adjusted by a single control member, such as sleeve (62), which encircles at least part of the housing member. The control member is coupled at least to the rotation means (and preferably also to the focusing means) by a magnetic linkage so as to permit rotation of the control member on the housing through at least one full revolution.

12 Claims, 2 Drawing Sheets

RETINOSCOPE WITH MAGNETIC COUPLING

FIELD OF THE INVENTION

This invention relates to retinoscopes, and more specifically to streak retinoscopes.

BACKGROUND TO THE INVENTION

Retinoscopy is a technique which employs a retinoscope to provide an objective indication of the refractive error of an eye. A retinoscope projects a patch of light onto the retina of an eye under examination, whilst permitting a user of the device to observe that patch. A streak retinoscope projects an elongated patch of light onto the eye, and includes a mechanism for rotating and focusing the patch. The rotation of the patch is used in the measurement of the axis of astigmatism of an eye under examination.

In a typical retinoscope, light emitted by a source passes through a focusing lens system, and is then reflected by an angled, half silvered or apertured mirror into the eye under observation. The image of the patch of light on the eye is viewed by the user from the opposite side of the mirror. The retinoscope also has a facility for moving the lens system to alter the focus (ie the vergence) of the patch of light on the retina of an eye under observation.

For ease of use, some retinoscopes have a single dual action control member for rotating the patch of light and for altering the position of the lens system. Such a member may, for example, comprise a rotary sleeve directly connected to the lens system and to a holder for a light source for the retinoscope. The sleeve is usually accessible through cut-outs in the outer housing of the retinoscope. Although the sleeve of this design can rotate through a full 360°, the portions of the body between the cut-outs limit the positions on the retinoscope at which the user can hold the sleeve. Other types of retinoscope have a sleeve which encircles the retinoscope housing, and is directly linked to the lamp holder and lens system through apertures in the housing. Whilst this arrangement provides a user with access to the sleeve through a full 360°, the cut-outs in the housing limit the extent of available rotational movement.

Other designs of retinoscope avoid this limitation by connecting an external sleeve, which encircles the retinoscope, to a lamp holder through a system of gears, but such an arrangement is relatively complicated and results in the patch of light being rotated in the opposite sense from the sleeve.

SUMMARY OF THE INVENTION

According to the invention, there is provided a streak retinoscope for projecting an elongate patch of light onto the retina of an eye under examination, the retinoscope comprising housing means, rotation means contained within the housing means and operable to rotate the patch relative to said eye, adjustable focusing means for focusing said patch on said eye, and a dual action external control member, which encircles at least part of the housing member, for operating the rotation means and adjusting the focusing means, wherein the control member is coupled to the rotation means by a magnetic linkage so as to permit rotation of the control member relative to the housing means through at least one full revolution.

Since the housing means is encircled by the control member, it does not impede access to the latter. Furthermore, the magnetic linkage enables the control member to move the rotation means without making direct mechanical contact with the latter, and thus avoids the need for any connecting gears or connections which limit the amount of allowable rotation of the control member.

Preferably, the control member is rotatably mounted on the housing means, and is also slidable therealong, the arrangement being such that rotation of the member operates the rotation means, whilst sliding movement of the member adjusts the focusing means.

Preferably, the magnetic linkage couples the control member to both the rotation means and the focusing means.

Preferably, the magnetic linkage comprises a first set of magnets connected to the control member (at angularly fixed positions relative thereto) and a second set of magnets connected to the rotation means (at angularly fixed positions) and to the focusing means. Thus, the magnetic linkage also avoids the need to provide a mechanical connection between the control member and the focusing means. Consequently, the focusing means and rotation means can both be situated wholly within the housing means, whilst the control member can be situated entirely outside the housing means.

Preferably, each set of magnets lies on a respective annular path, the two annular paths preferably being substantially concentric.

Preferably, the orientations of the magnets are such that any angular displacement of the first set of magnets relative to the second results in the exertion on the second set of magnetic attractive and repulsive forces tending to move the second set into its original angular position relative to the first set.

To that end, the polar orientations of the magnets in each set relative to the positions of the magnets in the other set preferably alternate.

Preferably, each magnet is so positioned that one of its poles faces the other set, and in this case, for each magnet, the pole facing the other set is of the opposite polarity to the correspondingly positioned pole of each of its immediate neighbours in its set.

Thus, for example, a magnet in the first set which is positioned with its north pole facing radially inwards towards a second set will be situated between two immediately neighbouring magnets, of the first set, whose south poles face radially inwards.

Preferably, there are six magnets in each set.

Preferably, the rotation means-causes the patch of light to rotate by rotating a lamp, and may therefore to advantage comprise a rotatable lamp holder and a rotatable inner sleeve which is angularly fixed to said holder and which carries said second set of magnets.

Conveniently, the control member comprises a cylindrical sleeve, on the inner periphery of which the magnets of said first set are mounted.

BRIEF DESCRIPTION OF THE DRAWINGS

The invention will now be described, by way of example only, with reference to the accompanying drawings in which.

DETAILED DESCRIPTION

Figure 1:
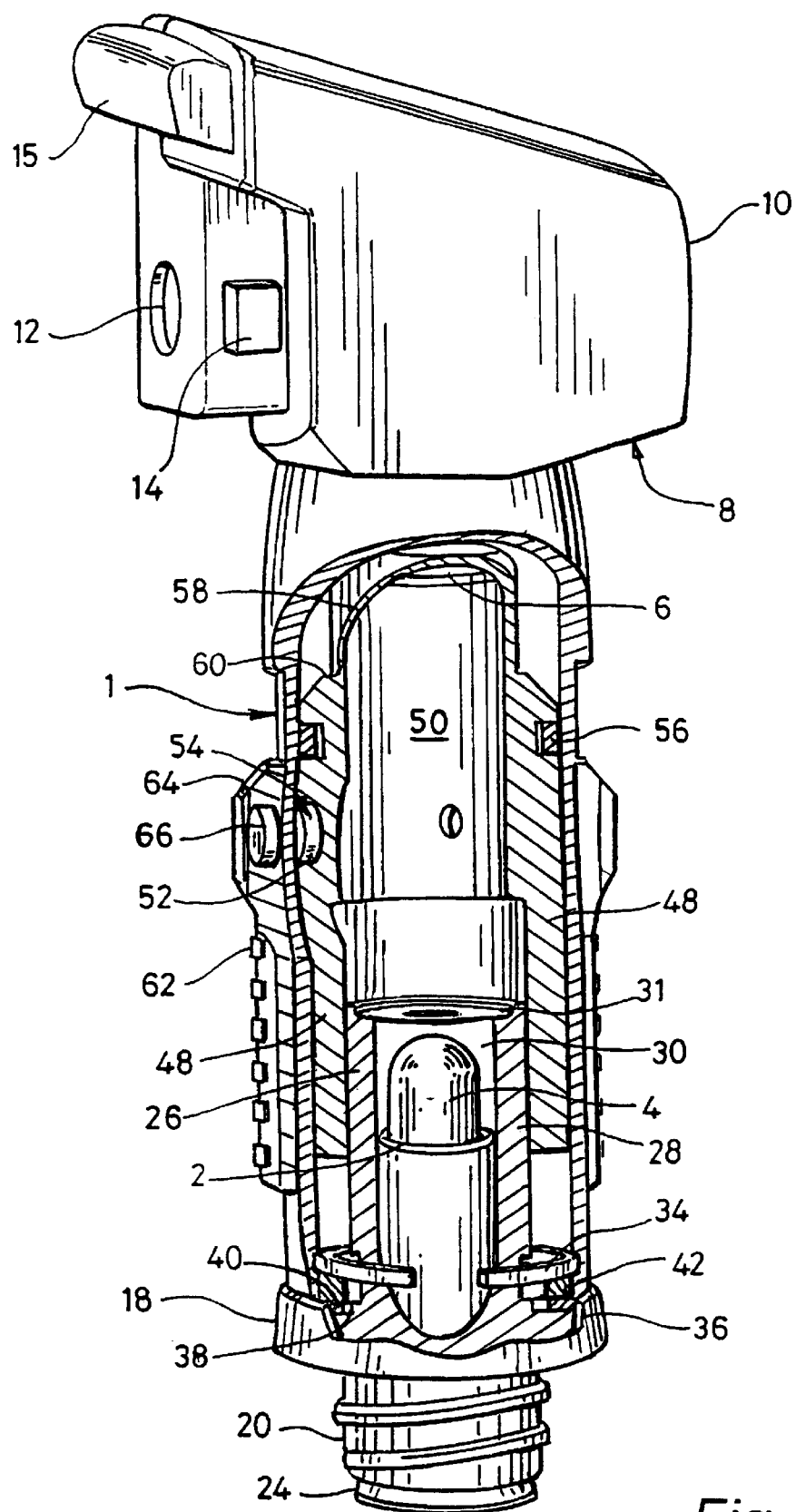
FIG. 1 is a partially cut-away side view of a streak retinoscope in accordance with the invention.

The streak retinoscope shown in the drawings has a housing comprising a cylindrical body 1 of a non ferromagnetic material (for example aluminium) which contains a lamp body 2 which carries having a halogen light bulb 4 having an elongate filament (not shown). In use, light emitted by the filament passes through a vergence lens system 6 situated towards the top of the body 1 and into a head 8. The head 8 is identical to the head used in the KEELER VISTA STREAK retinoscope, and includes an angled half-silvered or apertured mirror 9 which reflects light travelling up from the lens 6 through 90° to exit the head 8 through an aperture 11 in the front 10 thereof and into the eye under examination (not shown). The retinoscope forms an image of the filament of the bulb 4 on the eye under examination, and thus projects an elongate streak of light onto that eye. The image is viewed by the user of the retinoscope through the mirror 9 and a rear aperture 12. The housing also accommodates a plate which is moved by means of a button 14 and which includes two apertures, of different diameters, either of which can be selectively positioned in the viewing path from the mirror to the user to cause a selected degree of partial occlusion of the aperture 12 to occur.

The head is also equipped with an orbital/brow rest 15. The features of the head 8 are not described in detail because they are already known from the KEELER VISTA STREAK retinoscope.

The head 8 has a collar 16 which is externally screw-threaded and is screwed onto the top of the body 1. The bottom of the body 1 is externally screw-threaded so as to receive and retain a base cap 18. The base cap 18, in turn, includes a screw-threaded connector 20 for attachment to a handle (not shown), such as is used on the KEELER VISTA STREAK retinoscope, which handle also contains batteries for operating the lamp 2. The base cap 18 includes a through bore through which the lamp body 2 extends.

The bottom of the body 2, referenced 24, includes terminals for connecting the lamp 2 and hence the bulb 4 to a battery power supply in the handle. The lamp body 2 is securely held within an annular lamp holder 26 by means of an "O"-ring 27. The lamp holder 26 has an upstanding cylindrical wall 28 which defines a central passage 30 which accommodates the upper portion of the lamp. At the bottom of the wall 28, the holder 26 has a radial flange 36. The flange 36 is situated below a circlip 34 which sits in an annular groove on the inside of the body 1.

When the handle 21 is attached, the terminals in the handle make contact with the bottom 24 and exert an upward biasing force on the lamp 22, and hence on the holder 26. The flange 36 defines an annular upward shoulder 38 which is therefore urged against three balls 68, held in a race 40 which is in turn urged up against a thrust washer 42 located against the underside of the circlip 34. The lamp holder 26 also extends through the connector 20. The dimensions of the lamp holder are such that it, and hence the lamp body 2 (and bulb 4), is rotatable within the body 1 about the elongate axis of the latter.

A stop ring 31 is attached to the top of the wall 28, and serves to cut down glare from the edge of the bulb in the projected image.

Figure 2:
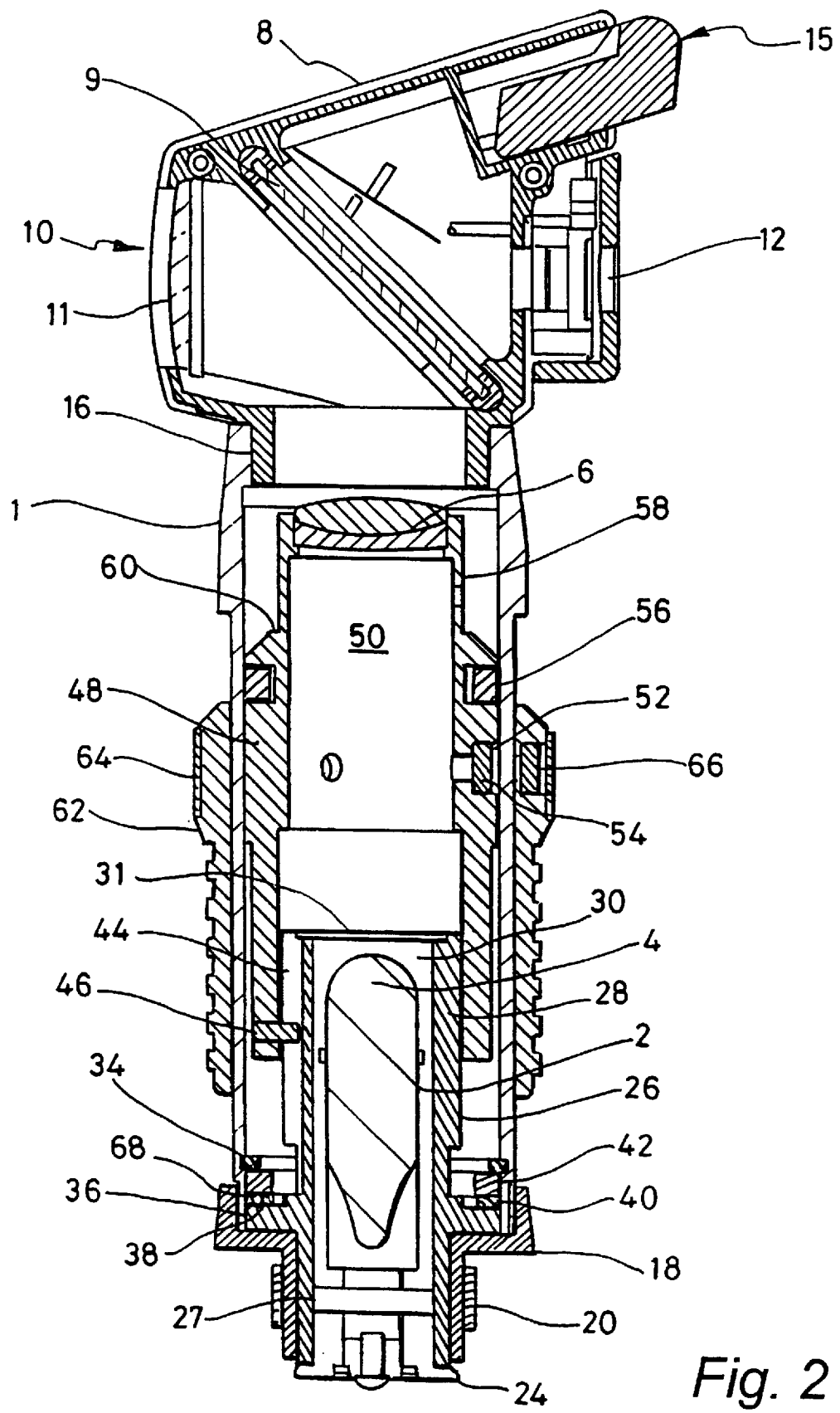
FIG. 2 is a sectional side view, from the opposite side, of the streak retinoscope.

The wall 28 of the lamp holder 26 includes an axial slot 44 into which a peg 46 extends (FIG. 2). The peg 46 projects radially inwards from an inner sleeve 48, which is rotatably retained in the body 1. The peg 46 provides a rotational key between the lamp holder 26 and the inner sleeve 48.

The inner sleeve 48 is also axially slidable along the inside of the body 1 and defines a central passage 50 for light from the bulb 4. The inner sleeve 48 also includes six equi-angularly spaced recesses in its outer surface. One such recess is shown at 52. Each of these recesses accommodates a respective rare earth magnet, such as the magnet 54. Each magnet is arranged with one pole facing radially outwards and the other radially inwards. Furthermore, the polar orientations of the magnets alternate so that each magnet which is orientated with its north pole facing outwards is positioned between two immediately neighbouring magnets which are positioned with their south poles facing outwards, and vice versa.

The outer surface of the sleeve 48 is also provided with an annular groove which accommodates a split washer 56 which, in use, presents a greater resistance to sliding of the sleeve 48 along the body 1 than it does to rotation of the sleeve 48 about the axis of the body 1. The top of the inner sleeve 48 includes a reduced diameter cylindrical portion 58 which extends upwards from an annular step 60, and to which the lens 6 is adhered.

The inner sleeve 48, and hence the lamp 22 and the lens 6 can be rotated and moved axially along the body 1 by means of a control member comprising an external sleeve 62 which is slidably and rotatably mounted on the exterior of the housing 1.

The sleeve 62 includes a trim ring 64 below which six rare earth magnets such as the magnet 66 are accommodated by the sleeve 62. The ring contains six magnets, each of which cooperates with a respective corresponding magnet mounted on the sleeve 48, and is in angular registry with the corresponding magnet in the sleeve 48. To that end the magnets are arranged in an annular formation, with the pole of each magnet which faces radially inwards being opposite to the pole of the corresponding magnet on the sleeve 48. Thus, a magnet in the sleeve 62 which is in angular registry with, and therefore cooperates with, a magnet (on the sleeve 48) orientated with its south pole facing outwards, will be arranged with its north pole facing radially inwards.

It will be seen that the magnets in the sleeve 62 and those mounted on the sleeve 48 provide a coupling between the sleeve 62 and sleeve 48 which acts through the wall of the body 1, and therefore avoids requirements for any apertures in the body 1 to provide a direct mechanical connection between the two components.

Also, since the sleeve 62 encircles the body 1, access to the sleeve 62 is not restricted by any part of the body 1.

In use, the orientation of the bulb 4 (and hence of the streak projected onto the eye under examination) is adjusted by rotating the sleeve 62 about the exterior of the body 1. This causes the magnets in the sleeve 62 to act on the magnets in the sleeve 48 so as to cause a corresponding rotation of the sleeve 48, and hence the lamp body 2 and lens system 6. While this happens, the split washer 56 prevents the sleeve 48 from sliding along the inside of the body 1 (and thus from altering the focus of the image on the eye under examination). If the focusing provided by the vergence lens 6 is to be adjusted, the sleeve 62 is slid axially along the housing 1, causing a similar axial movement of the inner sleeve 48, and hence the lens 6.

If, during rotational movement, the inner sleeve 48 and outer sleeve 62 begin to move out of registry with each other, then the attractive forces between each magnet in the ring 64 and its corresponding magnet on the sleeve 48 are supplemented by repulsive forces between each magnet in the ring 64 and one of the neighbours of the corresponding magnets on the sleeve 48. It will be appreciated that the rotation of the sleeve 62 causes the streak projected by the retinoscope to rotate in the same sense.

What is claimed is:

1. A streak retinoscope for projecting an elongate patch of light onto the retina of an eye under examination, the retinoscope comprising housing means, rotation means contained within the housing means and operable to rotate the patch relative to said eye, adjustable focusing means for focusing said patch on said eye, and a dual action external control member, which encircles at least part of the housing member, for operating the rotation means and adjusting the focusing means, wherein the control member is coupled to the rotation means by a magnetic linkage so as to permit rotation of the control member relative to the housing means through at least one full revolution.

2. The retinoscope according to claim 1, in which the control member is rotatably mounted on the housing means, and is also slidable therealong, the arrangement being such that rotation of the member operates the rotation means, whilst sliding movement of the member adjusts the focusing means.

3. The retinoscope according to claim 2, in which the magnetic linkage couples the control member to both the rotation means and the focusing means.

4. The retinoscope according to claim 1, in which the magnetic linkage comprises a first set of magnets connected to the control member at angularly fixed positions relative thereto and a second set of magnets connected to the rotation means at angularly fixed positions and to the focusing means.

5. The retinoscope according to claim 4, in which the focusing means and rotation means are both situated wholly within the housing means, whilst the control member is situated entirely outside the housing means.

6. The retinoscope according to claim 4, in which each set of magnets lies on a respective annular path, the two annular paths being substantially concentric.

7. The retinoscope according to claim 6, in which the orientations of the magnets are such that any angular displacement of the first set of magnets relative to the second results in the exertion on the second set of magnetic attractive and repulsive forces tending to move the second set into its original angular position relative to the first set.

8. The retinoscope according to claim 7, in which the polar orientations of the magnets in each set relative to the positions of the magnets in the other set alternate.

9. The retinoscope according to claim 8, in which each magnet is so positioned that one of its poles faces the other set, and for each magnet the pole facing the other set is of the opposite polarity to the correspondingly positioned pole of each of its immediate neighbours in its set.

10. The retinoscope according to claim 9, in which there are at least six magnets in each set.

11. The retinoscope according to claim 4, in which the rotation means causes the patch of light to rotate by rotating a lamp, and comprises a rotatable lamp holder and a rotatable inner sleeve which is angularly fixed to said holder and which carries said second set of magnets.

12. A retinoscope according to claim 1, in which the control member comprises a cylindrical sleeve, on the inner periphery of which the magnets of said first set are mounted.

* * * * *